United States Patent [19]

Nacharaju et al.

[11] Patent Number: 5,728,834
[45] Date of Patent: Mar. 17, 1998

[54] PROCESS FOR PREPARATION OF 4-ARYL-1,2,4-TRIAZOL-3-ONES

[75] Inventors: Krishnamurthy Nacharaju, Holland; James J. Springer, Saugatuck, both of Mich.

[73] Assignee: Wyckoff Chemical Company, Inc., South Haven, Mich.

[21] Appl. No.: 749,318

[22] Filed: Nov. 14, 1996

[51] Int. Cl.$^6$ ............... C07D 403/10; C07D 249/12
[52] U.S. Cl. ............... 544/366; 548/263.6; 548/264.6
[58] Field of Search ............... 548/263.6, 264.6; 544/366

[56] References Cited

U.S. PATENT DOCUMENTS

| | | |
|---|---|---|
| 1,796,403 | 3/1931 | Scheung et al. |
| 2,884,424 | 4/1959 | Klingberg ............... 260/308 |
| 2,898,343 | 8/1959 | Klingsberg ............... 260/308 |
| 3,647,814 | 3/1972 | Greenfield ............... 260/308 |
| 4,220,789 | 9/1980 | Gozzo et al. ............... 548/263 |
| 4,223,036 | 9/1980 | Heeres et al. ............... 424/269 |
| 4,259,504 | 3/1981 | Lang, Jr. et al. ............... 548/262 |
| 4,267,179 | 5/1981 | Heeres et al. ............... 424/25 D |
| 4,318,731 | 3/1982 | Kajioka et al. ............... 71/92 |
| 4,732,900 | 3/1988 | Weber et al. ............... 514/255 |
| 5,214,154 | 5/1993 | Theodoridis ............... 548/263.2 |
| 5,449,784 | 9/1995 | Goudar ............... 548/263.2 |

FOREIGN PATENT DOCUMENTS

| | | |
|---|---|---|
| 0301946 | 8/1988 | European Pat. Off. . |
| 0475898 | 9/1991 | European Pat. Off. . |
| 2531429 | 8/1982 | France . |
| 9303119 | 5/1994 | WIPO . |

OTHER PUBLICATIONS

Madding et al., Synthesis and X-ray Crystal Structure of A 2,4,5-Trisubstituted 1,2,4-Triazolin-3-One, Jul.-Aug. 1985, pp. 1121-1126.

*Primary Examiner*—Patricia L. Morris
*Attorney, Agent, or Firm*—Baker & Daniels

[57] ABSTRACT

A process for preparing 4-aryl-1,2,4-triazol-3-ones and 4-aryl-5-alkoxy-1,2,4-triazol-3-ones. A reaction mixture includes a primary aromatic amine, an alkyl carbazate and a trialkyl orthoformate. The reactants are heated in a reaction vessel in the presence of an acid catalyst and a polar solvent. After the reaction is complete, the solvent is removed, water is added, and the slurry is filtered to isolate 4-aryl-5-alkoxy-1,2,4-triazol-3-one. Alternatively, after the reaction is complete, an alkali metal alkoxide is added to the reaction mixture in the vessel, and the new mixture is again heated until the reaction is complete. The solvent is distilled from the mixture, and the remaining mixture is diluted with water. The slurry is separated from mixture, washed and dried to obtain 4-aryl-1,2,4-triazol-3-one in near 100% yield.

20 Claims, No Drawings

PROCESS FOR PREPARATION OF 4-ARYL-1,2,4-TRIAZOL-3-ONES

BACKGROUND OF THE INVENTION

The present invention relates generally to a process for preparation of 1,2,4-triazol-3-ones, and particularly to a process for the preparation of 4-aryl-1,2,4-triazol-3-ones.

The 1,2,4-triazol-3-one ring system is widely found in nature, as well as in a variety of synthetic products. Compounds containing this ring system have widespread application in fields such as the pharmaceutical industry. Modifying these triazols by adding substituents to the ring system can improve and expand the possible uses of the triazols. The 4-aryl substituents are particularly useful in the pharmaceutical industry, where they are utilized in products such as antidepressants and antihypertensive agents.

Several methods for constructing the 1,2,4-triazol-3-one ring system are known in the art. However, the known methods suffer from numerous drawbacks. For example, these known methods generally involve multi-step manipulations. Further, these methods often use expensive raw materials and/or harmful materials such as hydrazine. In addition, the known methods generally only provide a low overall yield of the triazolone product. Further, these methods often require high reaction temperatures and/or long reaction times in order to complete the reaction.

Several methods for preparing the 4-aryl-1,2,4-triazol-3-one derivatives are also known in the art. Many of these known methods use ethyl carbazate or hydrazine as a starting material. In one such method, formanilide is condensed with ethyl carbazate to form the desired triazolone ring structure. In this method, however, the yield is only about 3%. In another known method, formanilide is treated with phenylsulfonyl chloride to give the amide imidosulfonate intermediate. The intermediate is reacted with ethyl carbazate, and the product of this reaction is cyclized with base to the triazolone. In this case, the yield is only about 25%. In yet another method, ethyl carbazate is reacted with an alkyl amidate hydrochloride. The product of this reaction is isolated, condensed with aniline and thereafter cyclized with a base. The yield obtained by this method is about 40%. Another disadvantage with this method is that it gives the 5-alkyl-substituted triazalones.

Other known methods for the preparation of 4-aryl-1,2,4-triazol-3-ones involve the use of hydrazine as a raw material. In one such method, phenylurea is reacted with hydrazine to give a 4-phenylsemicarbazide. The semicarbazide is then condensed with ethyl formate to give the 4-phenyltriazolone. The overall yield from this method is about 20%. In another method, a 4-phenylsemicarbazide is reacted with formic acid to form the 1-formyl-4-phenylsemicarbazide intermediate, followed by intramolecular condensation to the 4-phenyltriazolone. The yield obtained by this method is about 40%. In yet another method, a substituted aniline is converted to the phenylcarbamate derivative. The phenylcarbamate is treated with hydrazine to give the phenylsemicarbazide derivative, followed by condensation with formamidine acetate to give the 4-phenyltriazolone. Each of these methods requires the use of the toxic compound hydrazine. In addition, the methods suffer from low overall yield.

European Patent Document EP-475,898-A1 discloses a process for the synthesis of 4,5-dialkyl triazol-3-ones, including several imidazole derivatives. Example II of this reference deals with the construction of a triazolone ring. The process described in this document takes place in two steps. An amine is initially reacted with a trialkyl orthoester to give the alkoxyimine intermediate. The intermediate is then reacted with ethyl carbazate to give the 4,5-dialkyl triazolone. The reaction times in this method are very long, on the order of ten to twelve hours for the first step, and twenty hours for the second step. Further, the triazolone ring described in this example includes a 4-alkyl instead of a 4-aryl, and an unwanted 5-alkyl substituent. In addition, the reaction only occurs at high temperatures. Therefore, high boiling solvents such as toluene and xylene are used.

An article by Madding, et al., J. Heterocyclic Chem., 22, 1121 (1985) discloses a process for synthesizing 4,5-disubstituted triazol-3-ones. In this process, an amide is reacted with phosgene, and the product of the reaction is further reacted with methyl carbazate. The product then undergoes base-induced intramolecular condensation to the triazol-3-one. This reaction scheme involves multiple steps, utilizes the toxic gas phosgene and also provides a ring structure having substituents at both the 4 and 5 positions.

EP-301,946-A3 discloses a method of making 1,2,4-triazol-3-ones from oxadiazolinones. As shown in scheme 4 of this reference, a monoacyl hydrazide is reacted with phosgene to form an oxadiazolinone. Upon reaction with an amine, the oxadiazolinone is then converted to an acylsemicarbazide, which is cyclized with NaOH or KOH to form the 1,2,4-triazol-3-one. This scheme also involves multiple steps and utilizes phosgene.

The known methods suffer from common disadvantages in that they generally utilize expensive reagents, require multiple steps, use toxic and/or dangerous compounds, require lengthy reactions and/or severe reaction conditions, and provide low yields.

Accordingly, it is desired to provide an improved process for preparation of 4-aryl-1,2,4-triazol-3-ones. The improved process must be cost effective, provide a high yield of product, use generally safe ingredients, require short reaction times and/or low temperatures, and enable the 4-aryl-1,2,4-triazol-3-ones to be produced in one reactor in an uninterrupted operation.

SUMMARY OF THE INVENTION

The problems of the prior art are addressed by the present invention, wherein a process for the preparation of 4-aryl-1,2,4-triazol-3-ones and 4-aryl-5-alkoxy-1,2,4-triazol-3-ones is provided. Briefly stated, the invention comprises a process for preparation of 4-aryl-1,2,4-triazol-3-ones and 4-aryl-5-alkoxy-1,2,4-triazol-3-ones that is performed in a single reactor vessel, provides a high yield of the desired triazolone, uses generally safe ingredients, and requires short reaction times at relatively mild reaction conditions.

The present invention, in one form thereof, provides a process for preparing 4-aryl-1,2,4-triazol-3-ones of the formula

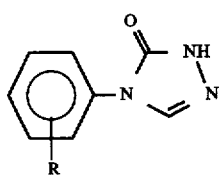

wherein R is hydrogen, nitrogen, a halogen, a primary, secondary or tertiary amine, a straight chain, branched or cyclic alkyl group, an alkoxy group, a substituted or unsubstituted aromatic group such as a phenyl, biphenyl, benzyl or naphthyl group, or a substituted or unsubstituted heteroaromatic group, such as a pyridyl group. A reaction mixture comprising (1) a primary aromatic amine of the formula

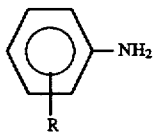

wherein R is the same as described above; (2) an alkyl carbazate of the formula

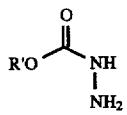

wherein R' is an alkyl group; (3) a trialkyl orthoformate of the formula

wherein R" is an alkyl group; (4) an acid catalyst; and (5) a polar solvent, is heated for a period of time sufficient to drive the reaction substantially to completion. An alkali metal alkoxide is added to the reaction mixture, and the heating continues for a period of time sufficient to drive the reaction substantially to completion. The solvent is distilled, water is added to the remaining mixture, and the mixture is acidified. The 4-aryl-1,2,4-triazol-3-one is filtered from the remainder of the mixture, and the filter cake is then washed with water and dried.

The invention further comprises, in another form thereof, a process for preparing 4-aryl-5-alkoxy-1,2,4-triazol-3-ones of the formula

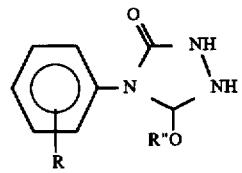

wherein R is the same as above. A reaction mixture comprising (1) a primary aromatic amine of the formula

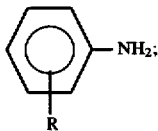

(2) an alkyl carbazate of the formula

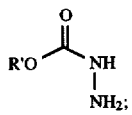

(3) a trialkyl orthoformate of the formula

wherein R, R' and R" are the same as above, (4) an acid catalyst; and (5) a polar solvent, is heated for a period of time sufficient to drive the reaction substantially to completion. The solvent is then distilled from the reaction mixture, and water is added to the resulting mixture. The 4-aryl-5-alkoxy-1,2,4-triazol-3-one is filtered from the remainder of the mixture, and the filter cake is then washed with water and dried.

An advantage of the present invention is that it provides a process for the preparation of 4-aryl-1,2,4-triazol-3-ones that may be performed in one pot, at low temperature, and under mild reaction conditions.

Another advantage of the present invention is that it provides a process for the preparation of 4-aryl-1,2,4-triazol-3-ones that provides high yields of the desired end product.

Yet another advantage of the present invention is that it provides a process for the preparation of 4-aryl-1,2,4-triazol-3-ones that avoids the use of harmful ingredients.

A further advantage of the present invention is that it provides a process for the preparation of specified 4-aryl-1,2,4-triazol-3-ones derivatives.

DETAILED DESCRIPTION OF THE INVENTION

The present invention provides a process for the preparation of 4-aryl-1,2,4-triazol-3-ones of the general formula:

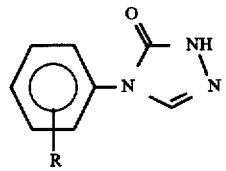

wherein R is hydrogen, nitrogen, a halogen, a primary, secondary or tertiary amine, a straight chain, branched or cyclic alkyl group, an alkoxy group, a substituted or unsubstituted aromatic group such as a phenyl, biphenyl, benzyl or naphthyl group, or a substituted or unsubstituted heteroaromatic group, such as a pyridyl group. R may be substituted at any ring position of the aromatic primary amine.

In the process of the present invention, the reaction takes place in a single reactor vessel, or "pot." Briefly stated, a primary aromatic amine is mixed with an alkyl carbazate and a trialkyl orthoformate in a polar solvent, and in the presence of an acid catalyst. The mixture is heated for about two hours, or until the reaction is complete. Preferably, the reaction is carried out at a temperature between about 40° and 100° C., and most preferably, between about 50° and 60° C. A base is added to the resulting mixture, and this mixture is once again heated at the reaction temperature for about two hours, or until the in situ reaction is complete. The solvent is removed from the reaction mixture, and the remaining mixture is cooled. Water is added to the mixture, the mixture is acidified, and the slurry is thereafter filtered from the solution. The filter cake is washed with water, and then dried. The 4-aryl triazolone derivative is produced in near 100% yield.

The aromatic amine used in the present invention is a primary aromatic amine of the general formula:

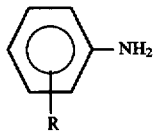

wherein R is hydrogen, nitrogen, a halogen, a primary, secondary or tertiary amine, a straight chain, branched or cyclic alkyl group, an alkoxy group, a substituted or unsubstituted aromatic group such as a phenyl, biphenyl, benzyl or naphthyl group, or a substituted or unsubstituted heteroaromatic group, such as a pyridyl group. R may be substituted at any ring position of the aromatic primary amine.

The alkyl carbazate is a compound of the general formula:

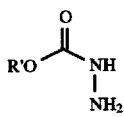

wherein R' is an alkyl group. Although the alkyl group may include higher numbers of carbon atoms, which carbon atoms may be present in a straight chain, branched or cyclic arrangement, alkyl groups having between 1 and 4 carbon atoms are preferred due to their availability. In addition, carbazates having lower alkyl groups are well known in the literature.

The trialkyl orthoformate is a compound of the general formula:

wherein R" is an alkyl group. Although this alkyl group may also include higher numbers of carbon atoms, which carbon atoms may be present in a straight chain, branched or cyclic arrangement, alkyl groups having between 1 and 4 carbon atoms are similarly preferred for use in the trialkyl orthoformates.

The acid catalyst can be any organic acid, organosulfonic acid or inorganic acid, although it is preferred to use an organosulfonic acid. The organosulfonic acid may be either an arylsulfonic acid, an alkylsulfonic acids, or a mixture of the two. p-toluenesulfonic acid is a particularly preferred acid catalyst due to its availability and cost.

The base is an alkali metal alkoxide. Particularly preferred bases are alkoxides such as sodium methoxide, sodium ethoxide and potassium tert-butoxide.

Virtually any polar solvent may be utilized for the reaction. Lower alcohol solvents such as methanol, η-propanol, n-butanol ethanol, isopropanol and tert-butanol are particularly preferred. Other polar solvents, such as aprotic solvents, may also be used with beneficial results. Examples of aprotic solvents that may be utilized include dimethyl sulfoxide (DMSO), N,N-dimethylformamide (DMF) and N-methylpyrrolidone (NMP).

Unlike methods for preparation of 1,2,4-triazol-3-ones known in the art, the present method only requires the use of about 1.05 molar equivalents, or less, of the alkyl carbazate and trialkyl orthoformate, with reference to the moles of the amine. As a result, the large excess of ingredients that is normally required in the processes known in the art is eliminated. Further, since the reaction between the primary aromatic amine, the alkyl carbazate and the trialkyl orthoformate goes to completion under the conditions described herein, the reaction gives nearly 100% yield of the triazolone.

The following examples are presented in order to more fully illustrate the process of the present invention:

EXAMPLES

1. Preparation of 2,4-Dihydro-4-phenyl-3H-1,2,4-triazol-3-one: A mixture of aniline (52.8 g, 0.56 mols), methyl carbazate (53.0 g, 0.59 mols), trimethyl orthoformate (62.5 g, 0.59 mols) and ρ-toluenesulfonic acid (2.0 g, 0.01 mols) in methanol (1000 mL) was heated at 50°-60° C. for 2 hours. 25% Sodium methoxide (171.7 g, 0.795 mols) in methanol was added slowly, and the mixture was heated to 50°-60° C. for another 2 hours. The methanol was distilled and the mixture was cooled to 20° C. Water (700 mL) was added, and the mixture was acidified to pH 1. The solid was filtered, and the filter cake was washed with water and then dried. 2,4-dihydro-4-phenyl-3H-1,2,4-triazol-3-one was produced in 99% yield. (90.0 g)

2. Preparation of 2,4-Dihydro-4-(4-chlorophenyl)-3H-1,2,4-triazol-3-one: A mixture of 4-chloroaniline (52.5 g, 0.41 mols), methyl carbazate (38.7 g, 0.43 mols), trimethyl orthoformate (45.58 g, 0.43 mols) and ρ-toluenesulfonic acid (1.65 g, 0.0086 mols) in methanol (1000 mL) was heated at 50°-60° C. for 2 hours. 25% Sodium methoxide (140.0 g, 0.64 mols) in methanol was added slowly, and the mixture was heated at 50°-60° C. for another 2 hours. The methanol was distilled and the mixture was cooled to 20° C. Water (700 mL) was added, and the mixture was acidified to pH 1. The solid was filtered, and the filter cake was washed with water and then dried. 2,4-dihydro-4-(4-chlorophenyl)-3H-1,2,4-triazol-3-one was produced in 99% yield. (79.0 g).

3. Preparation of 2,4-Dihydro-4-{4-[4-(4-methoxyphenyl)-1-piperazinyl]phenyl}-3H-1,2,4-triazol-3-one: A mixture of 4-[4-(4-methoxyphenyl)-1-piperazinyl] benzenamine (58.8 g, 0.20 mols), methyl carbazate (19.0 g, 0.21 mols), trimethyl orthoformate (22.5 g, 0.21 mols) and ρ-toluenesulfonic acid (0.5 g, 0.0026 mols) in methanol (1000 mL) was heated at 50°-60° C. for 2 hours. 25% Sodium methoxide (57.2 g, 0.265 mols) in methanol was added slowly, and the mixture was heated at 50°-60° C. for another 2 hours. The methanol was distilled (700 mL) and the mixture was cooled to 20° C. Water (700 mL) was added, and the resulting slurry was filtered. The filter cake was washed with water and then dried to produce the 2,4-Dihydro-4-{4-[4-(4-methoxyphenyl)-1-piperazinyl] phenyl}-3H-1,2,4-triazol-3-one product in ~100% yield. (72.0 g).

In order to prepare the 5-alkoxy substituent, it is not necessary to perform the in situ base treatment with the alkoxide. Following the completion of the reaction between the amine, the alkyl carbazate and the trialkyl orthoformate as described above, the reaction mixture is thereafter cooled to about 20° C., and water is added as before. The mixture is filtered to separate the solids from the aqueous mixture. The filter cake is washed with water, and then dried to provide the 4-aryl-5-alkoxy-1,2,4-triazol-3-one.

While this invention has been described in a preferred embodiment, the present invention can be further modified within the spirit and scope of this disclosure. This description is therefore intended to cover any variations, uses, or adaptations of the invention using its general principles. Further, this description is intended to cover such departures from the present disclosure as come within known or customary practice in the art to which this invention pertains and which fall within the limits of the appended claims.

What is claimed is:

1. A process for preparing 4-aryl-1,2,4-triazol-3-ones of the formula

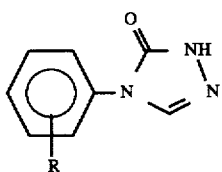

wherein R is hydrogen, a primary, secondary or tertiary amine, a straight chain, branched or cyclic alkyl group, an alkoxy group, or a substituted or unsubstituted aromatic group, wherein aryl means phenyl or naphthyl; and wherein substituted aromatic means an aryl group bearing a halogen, a primary, secondary or tertiary, amine, a straight chain, branched or cyclic alkyl group, or an alkoxy group;

the process comprising:

heating a reaction mixture comprising (1) a primary aromatic amine of the formula

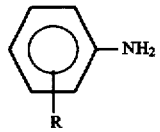

wherein R is the same as described above; (2) an alkyl carbazate of the formula

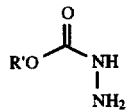

wherein R' is an alkyl group; (3) a trialkyl orthoformate of the formula

HC(OR")$_3$ wherein R" is an alkyl group; (4) an acid catalyst; and (5) a polar solvent, at a temperature and for a period of time sufficient to drive the reaction substantially to completion;

adding an alkali metal alkoxide to the reaction mixture, and heating the mixture at a temperature and for a period of time sufficient to drive the reaction substantially to completion; and separating the 4-aryl-1,2,4-triazol-3-one from the remainder of the mixture.

2. The process of claim 1, wherein R' is a lower alkyl group having between 1 and 4 carbon atoms.

3. The process of claim 1, wherein R" is a lower alkyl group having between 1 and 4 carbon atoms.

4. The process of claim 1, wherein the acid catalyst is an organosulfonic acid.

5. The process of claim 4, wherein the 4-aryl-1,2,4-triazol-3-one is 2,4-Dihydro-4-{4-[4-(4-methoxyphenyl)-1-piperazinyl]phenyl}-3H-1,2,4-triazol-3-one, and wherein the reaction mixture comprises 4-[4-(4-methoxyphenyl)-1-piperazinyl benzenamine, methyl carbazate, trimethyl orthoformate, and the acid catalyst is p-toluenesulfonic acid.

6. The process of claim 1, wherein the polar solvent is a lower alcohol selected from the group consisting of methanol, ethanol, isopropanol and tert-butanol, η-propanol and n-butanol.

7. The process of claim 1, wherein the polar solvent is an aprotic solvent selected from the group consisting of dimethyl sulfoxide, N,N-dimethylformamide and N-methylpyrrolidone.

8. The process of claim 1, wherein the alkali metal alkoxide is selected from the group consisting of sodium methoxide, sodium ethoxide and potassium tert-butoxide.

9. The process of claim 1, wherein the separating step comprises the steps of driving off the solvent, adding water to the resulting mixture, acidifying the mixture, and separating the 4-aryl-1,2,4-triazol-3-one from the mixture.

10. The process of claim 9, wherein the solvent is driven off by distillation, and the 4-aryl-1,2,4-triazol-3-one is separated by filtration.

11. The process of claim 1, wherein the heating steps take place at a temperature of between about 40° and 100° C.

12. The process of claim 11, wherein the temperature is between about 50° and 60° C.

13. A process for preparing 4-aryl-5-alkoxy-1,2,4-triazol-3-ones of the formula

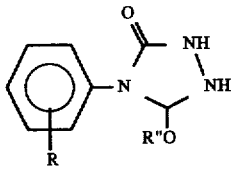

wherein R is hydrogen, a halogen, a primary, secondary or tertiary amine, a straight chain, branched or cyclic alkyl group, an alkoxy group, or a substituted or unsubstituted aromatic group, wherein aryl means phenyl or naphthyl; and wherein substituted aromatic means an aryl group bearing a halogen, a primary, secondary, or tertiary, amine, a straight chain, branched or cyclic group, or an alkoxy group;

the process comprising:

heating a reaction mixture comprising (1) a primary aromatic amine of the formula

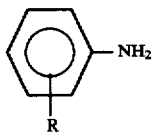

wherein R is the same as described above; (2) an alkyl carbazate of the formula

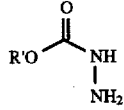

wherein R' is an alkyl group; (3) a trialkyl orthoformate of the formula

HC(OR")$_3$ wherein R" is an alkyl group; (4) an acid catalyst; and (5) a polar solvent, under reflux at a temperature and for a period of time sufficient to drive the reaction substantially to completion;

distilling the solvent from the reaction mixture;

adding water to the reaction mixture; and separating the 4-aryl-5-alkoxy-1,2,4-triazol-3-one.

14. The process of claim 13, wherein the 4-aryl-5-alkoxy-1,2,4-triazol-3-one is separated by filtration.

15. The process of claim 14, wherein the separated 4-aryl-5-alkoxy-1,2,4-triazol-3-one is washed with water, and then dried.

16. The process of claim 13, wherein the heating step takes place at a temperature of between about 40° and 100° C.

17. The process of claim 16, wherein the temperature is between about 50° and 60° C.

18. The process of claim 13, wherein R' and R" are lower alkyl groups having between 1 and 4 carbon atoms.

19. The process of claim 13, wherein the polar solvent is a lower alcohol selected from the group consisting of methanol, ethanol, isopropanol and tert-butanol, or an aprotic solvent selected from the group consisting of dimethyl sulfoxide, N,N-dimethylformamide and N-methylpyrrolidone.

20. The process of claim 13, wherein the acid catalyst is an organosulfonic acid.

* * * * *

UNITED STATES PATENT AND TRADEMARK OFFICE
CERTIFICATE OF CORRECTION

PATENT NO. : 5,728,834
DATED : March 17, 1998
INVENTOR(S) : Krishnamurthy Nacharaju et al.

It is certified that error appears in the above-indentified patent and that said Letters Patent is hereby corrected as shown below:

Claim 1, column 7, line 10, after "hydrogen," and before "a primary", add -- a halogen, --.

Claim 1, column 7, line 16, after "tertiary", delete ",".

Claim 5, column 7, line 59, replace "methoxypbenyl" with -- methoxyphenyl --.

Claim 13, column 8, line 36, after "secondary", delete ",".

Claim 13, column 8, line 36, after "tertiary", delete ",".

Signed and Sealed this

Second Day of June, 1998

Attest:

BRUCE LEHMAN

Attesting Officer

Commissioner of Patents and Trademarks